United States Patent

Pfeifer et al.

(10) Patent No.: US 11,649,502 B2
(45) Date of Patent: May 16, 2023

(54) EXOSOMAL MICRORNA IN SERUM AS AN INDICATOR FOR THE ACTIVATION OF BROWN AND BEIGE FAT TISSUE (BAT)

(71) Applicants: RHEINISCHE FRIEDRICH-WILHELMS-UNIVERSITÄT BONN, Bonn (DE); MAASTRICHT UNIVERSITY, Maastricht (NL)

(72) Inventors: Alexander Pfeifer, Bonn (DE); Joschka Buyel, Cologne (DE); Yong Chen, Wuhan (CN); Wouter Van Marken Lichtenbelt, Eijsden-Margraten (NL)

(73) Assignees: Rheinische Friedrich-Wilhelms-Universität Bonn, Bonn (DE); Maastricht University, Maastricht (NL)

( * ) Notice: Subject to any disclaimer, the term of this patent is extended or adjusted under 35 U.S.C. 154(b) by 56 days.

(21) Appl. No.: 17/025,345

(22) Filed: Sep. 18, 2020

(65) Prior Publication Data

US 2021/0095343 A1   Apr. 1, 2021

Related U.S. Application Data

(63) Continuation of application No. 15/752,792, filed as application No. PCT/EP2016/072988 on Sep. 27, 2016, now abandoned.

(30) Foreign Application Priority Data

Sep. 28, 2015 (EP) .................................. 15187038

(51) Int. Cl.

| C12Q 1/68 | (2018.01) |
| C12Q 1/6883 | (2018.01) |
| C12Q 1/6806 | (2018.01) |
| C12Q 1/686 | (2018.01) |
| A61K 31/36 | (2006.01) |

(52) U.S. Cl.
CPC ......... *C12Q 1/6883* (2013.01); *C12Q 1/6806* (2013.01); *C12Q 1/686* (2013.01); *A61K 31/36* (2013.01); *C12Q 2600/136* (2013.01); *C12Q 2600/158* (2013.01); *C12Q 2600/178* (2013.01)

(58) Field of Classification Search
CPC .... C12Q 1/6883; C12Q 1/6806; C12Q 1/686; C12Q 2600/136; C12Q 2600/158; C12Q 2600/178; A61K 31/36
See application file for complete search history.

(56) References Cited

U.S. PATENT DOCUMENTS

2013/0102487 A1   4/2013   Gironella I Cos et al.

FOREIGN PATENT DOCUMENTS

| CN | 104800860 A | 7/2015 |
| WO | 2010056337 A2 | 5/2010 |
| WO | 2010065156 A1 | 6/2010 |

OTHER PUBLICATIONS

Hilton, C. et al., "MicroRNAs in adipose tissue: their role in adipogenesis and obesity." International Journal of Obesity, Mar. 1, 2013, vol. 37, No. 3, pp. 1-8.
Keller, Pernille, et al., "Gene-chip studies of adipogenesis-regulated microRNAs in mouse primary adipocytes and human obesity." BMC Endocrine Disorders, Miomed Central LTD, Mar. 22, 2011, vol. 11, No. 1, pp. 1-11.
Navi, Babak B, et al., "Association Between Incident Cancer and Subsequent Stroke", Annals of Neurology (2015) vol. 77, No. 2, pp. 291-300.
Trajkovski, M. et al., "MyomiR-133 regulates brown fat differentiation through Prdm 16." Nat. Cell. Biol., Dec. 2012, vol. 14, No. 12, pp. 1330-1335, Abstract.
Wu, Yan, et al., "Identification of miR-106b-93 as a negative regulator of brown adipocyte differentiation." Biochemical and Biophysical Research Communications, Aug. 13, 2013, vol. 438, No. 4, pp. 575-580.

*Primary Examiner* — J. E. Angell
(74) *Attorney, Agent, or Firm* — Saliwanchik, Lloyd & Eisenschenk (57) ABSTRACT

The present invention relates to methods for detecting activation of a brown/beige fat cell or brown/beige adipose tissue (BAT) in a biological sample taken from a mammal to be diagnosed, comprising measuring the amount of miR-92 in said sample. The invention furthermore relates to diagnostic and clinical applications of the methods of the invention.

10 Claims, 6 Drawing Sheets

Specification includes a Sequence Listing.

EXOSOMAL MICRORNA IN SERUM AS AN INDICATOR FOR THE ACTIVATION OF BROWN AND BEIGE FAT TISSUE (BAT)

CROSS REFERENCE TO A RELATED APPLICATION

This application is a Continuation Application of U.S. patent application Ser. No. 15/752,792, filed Feb. 14, 2018; which is a National Stage Application of International Application Number PCT/EP2016/072988, filed Sep. 27, 2016; which claims priority to European Patent Application No. 15187038.3, filed Sep. 28, 2015, all of which are incorporated herein by reference in their entirety.

SEQUENCE LISTING

The Sequence Listing for this application is labeled "SeqList-12Feb18-ST25.txt", which was created on Feb. 12, 2018, and is 1 KB. The entire content is incorporated herein by reference in its entirety.

FIELD OF INVENTION

The present invention relates to methods for detecting activation of a brown/beige fat cell or brown/beige adipose tissue (BAT) in a biological sample taken from a mammal to be diagnosed, comprising measuring the amount of miR-92 in said sample. The invention furthermore relates to diagnostic and clinical applications of the methods of the invention.

BACKGROUND OF THE INVENTION

The obesity epidemic affects more than 2 billion people world-wide (Ng et al., 2014), but only very few anti-obesity drugs are available. Although brown adipose tissue might be a potential target for novel anti-obesity therapies, the identification or development of drugs that target human BAT is hampered by the lack of diagnostic tools.

Using fluorodeoxyglucose ($^{18}$F-FDG) PET/CT imaging, several groups identified metabolically active BAT in human adults (Cypess et al., 2009; Saito et al., 2009; van Marken Lichtenbelt et al., 2009; Virtanen et al., 2009). However, this technique requires activation of BAT and exposes patients to ionizing radiation.

Activation of brown adipose tissue (Bartelt et al., 2011) is mainly controlled by the sympathetic nervous system (Cannon and Nedergaard, 2004; Kajimura and Saito, 2013; Pfeifer and Hoffmann, 2014; Rosen and Spiegelman, 2014). Sympathetic nerves, as well as tissue-resident macrophages (Nguyen et al., 2011) release norepinephrine (NE) that activates beta adrenergic receptors and induces production of cyclic adenosine monophosphate AMP (cAMP) which in turn activates protein kinase A and lipolysis (Cannon and Nedergaard, 2004).

Apart from "classical" brown adipocytes, inducible brown adipocytes with thermogenic potential—also known as beige or brite (brown-like-in-white) adipocytes—have been identified in white adipose tissue (WAT) (Frontini and Cinti, 2010; Harms and Seale, 2013; Lo and Sun, 2013; Rosen and Spiegelman, 2014). "Browning" of WAT, i.e. increasing the number of beige/brite adipocytes, can be induced by a large spectrum of substances and stimuli (Pfeifer and Hoffmann, 2014) including cold exposure and NE treatment, as well as adenosine (Gnad et al., 2014) and cyclic guanosine monophosphate (Bordicchia et al., 2012; Mitschke et al., 2013).

The metabolically active fat depots in the neck and supraclavicular region of human adults contain both constitutive brown and inducible beige adipocytes (Jespersen et al., 2013; Sharp et al., 2012; Wu et al., 2012) with deeper neck depots possessing classical brown characteristics and more superficial depots expressing beige markers (Cypess et al., 2013). Thermogenesis mediated by both brown and beige/brite adipocytes is dependent on the action of the uncoupling protein 1 (UCP-1) (Shabalina et al., 2013), which uncouples mitochondrial ATP production and is stimulated by fatty acids that are liberated by lipolysis (Cannon and Nedergaard, 2004).

US 2013-331433 discloses a method of modulating respiratory chain uncoupling in a cell or thermogenesis in a tissue comprising contacting the cell or tissue with a miRNA agent that modulates activity of at least one mitochondrial uncoupler.

miRNAs are small non-coding RNAs, which regulate protein expression in a broad range of tissues including brown adipose tissue (Trajkovski and Lodish, 2013). The miRNA expression patterns of brown adipocytes are significantly altered during differentiation and after cold-exposure (Chen et al., 2013; Trajkovski et al., 2012; Walden et al., 2009).

WO 2013/063519 discloses a method for evaluating a pancreatic cyst in a patient comprising measuring from a pancreatic cyst sample from the patient the level of expression of at least two of the following biomarker miRNAs: miR-24, miR-30a-3p, miR-92a, miR-18a, miR-342-3p, miR-99b, miR-106b, miR-142-3p, or miR-532-3.

miRNAs can be released into the blood, and it is known that alterations in the levels of circulating miRNAs can be used for diagnostic purposes (Cortez et al., 2011). The power of serum miRNAs as diagnostic tools has been clearly demonstrated for cancer (Erase et al., 2010; Rosenfeld et al., 2008). miRNAs can also be secreted via lipid-based carriers, such as exosomes, that provide a protective vesicle against degradation of transported miRNA by RNase (Cheng et al., 2014; Thery et al., 2002: van Niel et al., 2006).

Bonauer et al. (in: Bonauer A, et al. MicroRNA-92a controls angiogenesis and functional recovery of ischemic tissues in mice. Science. 2009; 324:1710-1713) disclose that miR-92a appears to target mRNAs corresponding to several proangiogenic proteins, including the integrin subunit alpha5, and thus may serve as a valuable therapeutic target in the setting of ischemic disease.

WO 2014/201314 discloses a method of regulating Brown Adipose Tissue activation and differentiation in a subject, the method comprising contacting one or more cells in the subject with a composition comprising one or more exogenous miRNA-455, the cells being selected from the group consisting of brown adipose cells, white adipose cells and preadipocytes.

PCT/US2014/010173 and Enderle et al. (in: Enderle et al., (2015) Characterization of RNA from Exosomes and Other Extracellular Vesicles Isolated by a Novel Spin Column-Based Method. PLoS ONE 10(8): e0136133. doi:10.1371/journal.pone.0136133) describe the development and characterization of a spin column-based method for the isolation of total RNA from extracellular vesicles in serum and plasma. hsa-miR-92a-3p is determined, but disclosed as being independent from vesicles (Arroyo J D, Chevillet J R, Kroh E M, Ruf I K, Pritchard C C, Gibson D F, et al. Argonaute2 complexes carry a population of circulating microRNAs independent of vesicles in human plasma. PNAS USA. 2011 Mar. 22; 108(12):5003-8).

Because of the fact that the major focus of brown adipose tissue research has been on pathways that regulate UCP-1-mediated energy expenditure to identify potential brown adipose tissue-centered therapies, diagnostic tools that allow for safe and easy assessment of brown adipose tissue in humans are lacking.

BRIEF SUMMARY

It is therefore an object of the present invention to provide an effective tool to detect the activity of brown/beige fat in the body, and to furthermore avoid the both laborious and unhealthy measures that are currently undertaken in order to analyze fat in the body. The method should also be useful in a high-throughput format. Further objects and advantages of the present invention will become apparent to the person of skill when studying the following more detailed specification of the present invention.

In a first aspect of the present invention, this object is solved by a method for detecting activation of a brown/beige fat cell or tissue (BAT) in a biological sample taken from a mammal to be diagnosed, comprising measuring the amount of miR-92 in said sample, wherein said amount is reduced in activated BAT when compared to non-activated BAT.

To date, there is no biomarker for BAT that can be accessed based on a biological sample, such as blood or serum. It was found that brown adipocytes secrete exosomes, and that the exosomal miRNAs can be used as a biomarker for BAT activity in mammals, in particular humans and mice. The inventors show that brown adipocytes release miRNAs in exosomes and that BAT activation alters the exosomal miRNA pattern. Comparison of exosomal miRNAs isolated from mouse serum and brown adipocytes revealed that the abundance of seven miRNAs was commonly changed after BAT activation in vivo and in vitro. Importantly, one of these miRNAs—miR-92a—was also present in human serum exosomes and inversely correlated with BAT activity measured by $^{18}$F-FDG positron emission tomography coupled with computer tomography (PET/CT). Thus, exosomal miR-92a is the first serum biomarker correlating with human BAT activity.

Currently, PET/CT in combination with the radioactive tracer $^{18}$F-FDG is used. The drawbacks of this method are that the patient is a) exposed to a radioactively labelled substance ($^{18}$F-FDG); b) has to undergo a CT-X-ray exam; and c) is exposed to 1-1.5 h of cold, in order to allow an uptake of the radioactively labelled glucose into metabolically active areas, such as the brown fat. Furthermore, because of costs and the exposure to radiation only very few patients can be examined.

The present invention overcomes all of the above problems, as the test is performed using a sample (e.g. serum), and does not need any cold exposure.

Preferred is a method according to the present invention, wherein said amount of miR-92 negatively correlates with the activation/activity of said BAT. It was found that the marker does not only identify activation of BAT, but that miR-92 (especially Has-Mir-92a-3p) also correlates with the extent of the activation, a feature that can be used in particular to detect changes in the activation of BAT.

A second aspect of the present invention then relates to a method for detecting a patient suffering or likely to suffer from a disease related to BAT-activation, such as metabolic diseases, comprising measuring the amount of miR-92 in a biological sample taken from said patient to be diagnosed, wherein an amount of miR-92 that is the same or higher when compared to an activated BAT is indicative for a disease related to BAT-activation.

A third aspect of the present invention then relates to a method for identifying a compound that promotes or reduces the activation of a brown/beige fat cell or tissue (BAT), comprising a) contacting a candidate compound with BAT in a biological sample, b) measuring the amount of miR-92 derived from said BAT, and c) identifying a compound that promotes or reduces the activation of BAT based on the amount of said miR-92 produced in response to said candidate compound.

The methods as described herein can be performed in vitro and/or in vivo, either in a patient or test animal. The sample to be used can be any suitable sample containing miR-92 derived from BAT, either directly from the cells or tissue or "indirectly" through the isolation of cellular components or excreted microvesicles, such as exosomes. Thus, preferred is a method according to the present invention, wherein said sample is selected from a sample comprising fat cells, adipose tissue, blood, serum, a sample comprising exosomes, and a sample comprising exosomes derived from BAT. The sample can be obtained from the same patient over a period of time (e.g. during the course of treatment) or from different patients (e.g. diseased vs. non-diseased) or even be pooled sample (e.g. from groups of patients).

The mammal to be examined can be any kind of mammal, such as a mouse, monkey, rat, human, dog, cat, cow, pig, horse, sheep, goat, and rabbit. Preferred are dog, cat, pig, and human.

As mentioned above, it was found that the marker according to the invention (miR-92, and in mice, miR-34c*) is an indicator for the activity of BAT independently from cold-treatment. Thus, preferred is a method according to the present invention, wherein said activation/activity of said BAT is found independently from temperature (thermoneutrality). Nevertheless, the marker can also be induced by an extended exposure to cold, and, more interestingly, also by a short-term exposure to cold or a chemical substance, such as, for example, or CL-316,243 or other (3-adrenergic agonists. Thus, compounds can be identified having an effect on the activity of miR-92, in turn reflecting the activation of BAT (see below).

Any suitable method for the detection of miR-92 (and other miR's) can be used in the context of the present invention. Preferred is a method according to the present invention, wherein said detection comprises at least one method selected from nucleic acid reverse transcription, amplification, and detection, preferably PCR, such as quantitative PCR (qPCR). Nevertheless, numerous methods have been adopted for the detection and characterization of small RNAs, which is challenging due to their short length and low level of expression. These include molecular biology methods such as real-time RT-PCR, northern blotting, hybridization to microarrays, cloning and sequencing, as well as single cell miRNA detection by microscopy with in situ hybridization (ISH), including its fluorescent version (FISH). Resnick et al. (in: Resnick et al. The detection of differentially expressed microRNAs from the serum of ovarian cancer patients using a novel real-time PCR platform. Gynecologic Oncology 112 (2009) 55-59) disclose a high-throughput method. Tian T et al. (in: A review: microRNA detection methods. Org Biomol Chem. 2015 Feb. 28; 13(8): 2226-38) summarize and discuss newly developed miRNA detection methods.

As already mentioned above, recent demonstrations of metabolically active brown fat depots in adult humans have revolutionized current therapeutic approaches for obesity-related diseases. The balance between white adipose tissue (WAT) and BAT affects the systemic energy balance and is widely believed to be the key determinant in the development of obesity and related metabolic diseases (Singh R et al. Regulation of brown adipocyte metabolism by myostatin/follistatin signaling. Front Cell Dev Biol. 2014 Oct. 16; 2:60). Furthermore, BAT also plays roles in cardiovascular disease (Boon M R et al. High prevalence of cardiovascular disease in South Asians: Central role for brown adipose tissue? Crit Rev Clin Lab Sci. 2015 June; 52(3):150-7. Epub 2015 May 8).

Consequently, a marker indicating activation of BAT has a wide use in the field of these diseases, and thus a method according to the present invention is preferred, wherein said sample is derived from a patient suffering or likely to suffer from an obesity-related disease, diabetes and/or a cardiovascular disease, such as a stroke.

Similarly, in this context the invention provides a method as described herein for detecting a patient suffering or likely to suffer from a disease related to BAT-activation, comprising measuring the amount of miR-92 in a biological sample taken from said patient to be diagnosed, wherein an amount of miR-92 that is the same or higher when compared to an activated BAT is indicative for a disease related to BAT-activation. Preferred is a method according to the present invention, wherein said sample is derived from a patient suffering or likely to suffer from a metabolic disease, such as an obesity-related disease, diabetes and/or a cardiovascular disease, such as a stroke.

In one particular aspect, the method according to the present invention further comprises a monitoring of the amount of said miR-92 in biological samples taken from said patient. As mentioned, in one embodiment the sample(s) can be obtained from the same patient over a period of time (e.g. during the course of treatment) or from different patients (e.g. diseased vs. non-diseased) or even be pooled sample (e.g. from groups of patients).

Yet another aspect of the present invention then relates to a method for identifying a compound that promotes or reduces the activation of a brown/beige fat cell or tissue (BAT), comprising a) contacting a candidate compound with BAT in a biological sample, b) measuring the amount of miR-92 derived from said BAT, and c) identifying a compound that promotes or reduces the activation of BAT based on the amount of said miR-92 produced in response to said candidate compound. Preferred is a method according to the present invention, wherein said amount of said miR-92 as produced is compared with miR-92 in a non-activated BAT or a BAT before the contacting step.

Certain methods of identifying (screening) are known in the art and are discussed, e.g., in: In vitro Methods in Pharmaceutical Research, Academic Press, 1997; and in U.S. Pat. No. 5,030,015. Preferred is a method for screening according to the present invention, wherein said compound that promotes or reduces the activation of BAT based on the amount of said miR-92 produced in response to said candidate compound is present in a compound library, e.g. of "small molecules" or "bioactive small molecules" (usually defined as having a weight of less than 900 Daltons), a phage display library, or in a library of antibodies. These libraries, their production and their screening in order to identify the compound are known to the person of skill. Some libraries can be bought commercially and screened using machinery, such as robots.

The assays to determine the activation of a brown/beige fat cells or tissue (BAT) are described herein and consequently involve detecting the amount of the miR-92 produced in response to said candidate compound.

Another aspect of the present invention then relates to the candidate compound as identified or screened according to the method according to the present invention, which constitutes a candidate for and/or a BAT activation agent. This compound, according to the present invention, can be formulated into a pharmaceutical composition in a method for producing a pharmaceutical composition, comprising a method for identifying as above, and formulating said agent together with a pharmaceutically acceptable carrier, excipient, and/or stabilizer.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyl-dimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Preferred is a method according to the present invention, wherein said compound as identified is selected from small chemical molecules (see above), peptides, and antibodies and fragments thereof, which can be selected from a monoclonal, polyclonal, human, humanized, and/or recombinant antibody or a functional fragment thereof, optionally comprising a label.

Yet another important aspect of the present invention then relates to a pharmaceutical composition or formulation, produced according to a method according to the present invention as above containing the compound as a diagnostic agent and/or therapeutic agent. Said pharmaceutical composition or formulation further contains a pharmaceutically acceptable carrier, excipient, and/or stabilizer. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyl-dimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Yet another important preferred aspect of the present invention then relates to a diagnostic kit, comprising a compound as identified according to the present invention, optionally together with additional auxiliary agents for performing a method according to the present invention as above. The kit preferably contains the chemical substances, dyes, buffers, and the like that are required to perform the methods according to the present invention. The kit can also contain protein chips or microarrays for the analysis, as well as manuals and software and machinery in order to display and interpret the results of the diagnosis.

Another important preferred aspect of the present invention then relates to a method for treating a patient suffering or likely to suffer from a disease related to BAT-activation, comprising administering a therapeutically effective amount of a compound as identified according to the present invention, or a pharmaceutical composition or formulation according to the present invention to said patient.

"Treatment" as used herein refers to both therapeutic treatment and prophylactic or preventative measures, wherein the object is to prevent or slow down (lessen) the targeted pathologic condition or disorder, in particular an obesity-related disease, diabetes and/or a cardiovascular disease, such as a stroke. Those in need of treatment include those already with the disorder as well as those prone to have the disorder or those in whom the disorder is to be prevented. The treatment can both include adjuvant treatments and first line treatments of treatment-naive patients, and can be combined with other anti-obesity strategies, such as chemotherapies. Preferably, said treatment in said patient is for the treatment of obesity and/or diabetes.

Another important preferred aspect of the present invention then relates to a method for activating BAT in a patient suffering or likely to suffer from an obesity-related disease, diabetes and/or a cardiovascular disease, such as a stroke, comprising administering a therapeutically effective amount of a compound as identified according to the present invention, or a pharmaceutical composition or formulation according to the present invention to said patient.

The detection of BAT currently relies on PET/CT imaging of $^{18}$F-FDG uptake into metabolically active BAT. This imaging technique was originally developed—and is still mainly used—for detection of metastasis in oncology. Coincidentally, $^{18}$F-FDG-PET/CT imaging revealed the increased uptake of tracer in a region extending from the anterior neck to the thorax (Nedergaard et al., 2007). Several seminal papers (Cypess et al., 2009; Cypess et al., 2013; Saito et al., 2009; van Marken Lichtenbelt et al., 2009; Virtanen et al., 2009) showed that these areas of cold-induced glucose uptake correspond to BAT. However, the major drawback of this technique is the exposure of patients to ionizing radiation by both the FDG tracer and CT. In addition, patients need to be exposed to cold in order to activate BAT, which is problematic as it causes discomfort and has been linked with severe cardiovascular side-effects: Exposure to cold is associated with a statistically significant increased risk of myocardial events (Analitis et al., 2008; Bhaskaran et al., 2009). Thus, the use of $^{18}$F-FDG-PET/CT is especially problematic in obese patients that might suffer from cardiovascular disease, a major co-morbidity of obesity and type 2 diabetes.

Therefore, diagnostic markers of BAT are of great importance to study the role of human BAT in metabolic diseases as well as for clinical trials to stratify subjects and to measure the effects of drug candidates on BAT. In this respect, the relation between exosomal miR-92a abundance in human blood samples and cold-induced BAT activity is highly promising, especially since these blood samples were taken at thermoneutrality. As such, miR-92a represents a thermoneutral brown/beige fat biomarker for basic science and clinical applications, which can be measured with relative ease in large cohorts of patients.

The present invention will now be described further in the examples, nevertheless, without being limited thereto. For the purposes of the present invention, all references as cited here herby incorporated by reference in their entireties. The Figures show:

DETAILED DESCRIPTION

Examples

Experimental Procedures
Study Approval

The human study was approved by the ethics committee of Maastricht University Medical Centre, and all subjects provided written informed consent. All procedures were conducted according to the principles of the Declaration of Helsinki. All animal experiments were approved by the Animal Welfare Officers of University Medical Center Hamburg-Eppendorf (UKE) and Behörde fur Gesundheit und Verbraucherschutz Hamburg and the Landesamt fur Natur, Umwelt und Verbraucherschutz Nordrhein-Westfalen.

Statistics

Values are presented as means+/−standard error of means (SEM). Statistical differences were determined using Student's t-test (unpaired, two-tailed), or one-way ANOVA. GraphPad Prism 5 or Excel software was used to calculate P-values (*p<0.05). For human serum samples, statistical analyses were performed with SPSS Statistics 20.0 for MAC (IBM, Amonk, N.Y.). Human serum miR-92a and miR-133a expression levels were not normally distributed according to Shapiro-Wilk test. Therefore, these data were $\log_{10}$ transformed, which resulted in normal distribution, and analyzed accordingly. Two-sided independent sample t-tests were used to compare miRNA expressions between groups. Pearson correlations were used to identify correlations between variables. The level of statistical significance was set at p<0.05.

Animals

C57BL/6J wild type mice were purchased from Charles River Laboratories. Cold exposure was performed by housing 12 week old male mice at 4° C. for 7 days. The $\beta_3$-adrenergic agonist CL-316,243 (#1499, Tocris, Wiesbaden, GER, 0.2 mg/mL in 0.9 W/V % NaCl) was administered by subcutaneous injection (1 μg per g body weight) for 7 days. Control-treated C57BL/6J mice received vehicle injections (0.9% NaCl) correspondingly. Blood collections were performed after 4 hours of fasting. Mice were anesthetized with a mix containing Ketamin (25 mg/mL)/Xylazin (0.2%) in 0.9% NaCl, and blood was withdrawn transcardially.

miRNA Profiling qPCRs of exosome-derived miRNAs were performed with TaqMan Rodent MicroRNA Array card A and card B (M444909, Life-technologies, Carlsbad, Calif.). Mouse serum samples were pooled (3 mice per group) and 2 pools were analyzed per condition (cold, CL or wild type); for the analysis of brown adipocyte-derived exosomes, the supernatant of 6 wells from a 6-well plate was pooled from cells treated with 8-bromoadenosine 3',5'-cyclic monophosphate (cAMP; 200 μM) and untreated control cells. Data were analyzed with software RQ manager 1.2.1 and DataAssist v3.01 (Life-technologies, Carlsbad, Calif.).

Exosomal miRNAs that were deregulated more than 2-fold (compared to vehicle-injected mice) after CL-316, 243-treatment or cold-exposure, as well as those miRNAs up- or down-regulated 2-fold after cAMP treatment (as compared to control cells), were considered for the Venn diagram analyses. Selected candidates were validated with TaqMan miRNA assay kit according to the manufacturer's instructions.

Cell Culture

Interscapular brown pre-adipocytes were isolated from newborn mouse pups and differentiated in vitro with hormonal cocktail as previously described (Chen et al., 2013). Isolation and cultivation of primary white adipocytes was performed as described (Chen et al., 2013). 3T3-L1 (American Type Culture Collection, Rockville, Md.) were cultured as previously described (Mitschke et al., 2013). HepG2 were cultured in growth medium (DMEM with pyruvate 40% FBS, 1% P/S until fully confluent. $C_2C_{12}$ myoblasts (CRL-1772, ATCC, Molsheim Cedex, FR) were grown in DMEM with pyruvate, 10% FBS, 1% P/S until 80% confluent. $C_2C_{12}$ myocytes were fully differentiated as follows: 120.000 cells were seeded per well in DMEM with pyruvate 10% FBS, 1% P/S until confluent then cultured for 7 days in DMEM without pyruvate, 2% Horse Serum, 1% P/S and 1% non-essential amino acids solution, NEAA (Cat. No. 11140-050, Life-Technologies, Carlsbad, Calif.). All cells were kept in DMEM with 2% Exo-FBS (#FBSHI-250A-1, System Biosciences) 1% PS for 48 h either with or without 200 μM cAMP to release exosomes. The supernatant was withdrawn and used for exosome isolation.

Exosome Isolation

C57BL/6J wild type mice were purchased from Charles River Laboratories. Cold exposure was performed by housing 8 week old male mice at 18° C. for 7 days followed by 4° C. for 7 days. Blood was withdrawn transcardially after 4 hours fasting and subsequently sacrificing the mice. Organs (brain, liver, BAT, WATi, WATg and the soleus muscle) were obtained, washed in ice cold PBS and weighed. Tissues were incubated in 2 ml medium (DMEM with 2% Exo-FBS (#FBSHI-250A-1, System Biosciences, Mountain View, Calif.) 1% P/S) and chopped with scissors. The chopped tissue was centrifuged at 1,000 g for 5 minutes at RT and re-dissolved in medium and incubated for 30 minutes at 37° C., 5% $CO_2$. After another medium exchange the tissues were incubated for 2 hours at 37° C., 5% $CO_2$ to release exosomes. The supernatant was then withdrawn and used for exosome isolation. The exosomal samples used for qPCR and ELISA were adjusted to 1.65 mg and 16.5 mg tissue, respectively, to compare exosome/miR-92a release from various tissues. Isolation of exosome either from BA, BAT or serum was performed using exosome precipitation kit according to the manufacturer's instruction (#4478359 or #4478360, Lifetechnologies, Carlsbad, Calif.).

Exosomal RNAs were isolated according to the manufacturer's instructions (#4478545, Life-technologies, Carlsbad, Calif.). CD63 quantification was done with an ELISA-kit according to the manufacturer's instructions (#EXOEL-CD63A-1, System Biosciences, Mountain View, Calif.).

Western Blotting

Proteins from exosomes, cells and tissues were extracted with RIPA-lysis buffer (150 mM NaCl, 50 mM Tris-HCl, pH 7.5, 1% Nonidet P40, 0.25% Na-deoxycholate, 0.1% SDS) containing complete protease inhibitor cocktail (#04693116001, Roche, Basel, CH), 1 mM $Na_3VO_4$ and 10 mM NaF. Western blotting was performed with anti-CD63 (1:1,000), anti-Hsp70 (1:1,000), anti-CytoC (1:1,000) antibodies that were purchased from System Biosciences (#EXOAB, Mountain View, Calif.) or Santa Cruz (#sc-7159, Heidelberg, GER). Anti-α-Tubulin (1:1,000) antibody was purchased from Upstate (#DLN-09993, Lake Placid, N.Y.) and served as loading control.

Electron Microscopy

The exosomes were incubated with 3.5% uranyl acetate and visualized with Philips CM10 electron microscope (Philips, Amsterdam, NL).

Subjects miRNA expression levels were determined in thermoneutral blood samples from 22 randomly selected young, healthy subjects (Table 1) from two previously published studies, in which cold-stimulated BAT activity was measured as described previously (Hanssen et al., 2015; van der Lans et al., 2013). Briefly, mean BAT activity (expressed as SUVmean) was determined in manually outlined regions of interest using a threshold of 1.5 SUV and Hounsfield units between −10 and −180 to define BAT. When supraclavicular fat tissue activity did not exceed the threshold of 1.5 SUV, fixed volumes of interest were used to quantify tissue activity (van der Lans et al., 2014).

Ten subjects were additionally exposed to a 10-day cold acclimation protocol (van der Lans et al., 2013), after which miRNA expression levels were reassessed.

TABLE 1

Human subject characteristics and BAT activity

|  | All subjects (n = 22) | High BAT (n = 11) | Low BAT (n = 11) |
| --- | --- | --- | --- |
| Males/Females | 10/12 | 7/4 | 3/8 |
| Age (years) | 21.5 ± 2.3 | 20.8 ± 2.1 | 22.1 ± 2.5 |
| Weight (kg) | 66.0 ± 8.2 | 65.5 ± 6.8 | 66.4 ± 9.8 |
| BMI (kg/m$^2$) | 21.3 ± 1.7 | 21.0 ± 1.7 | 21.5 ± 1.7 |
| Fat % | 21.9 ± 8.1 | 18.2 ± 6.7 | 25.6 ± 7.8* |
| BAT activity (SUVmean) | 2.38 ± 0.77 | 2.93 ± 0.17 | 1.82 ± 0.74* |

Data are presented for all subjects together and the high BAT and low BAT group separately.
Values are expressed as means +/− SD (*p < 0.05, high BAT vs. low BAT)

Detection of miR-92a in Exosomes from Human Serum

After extraction, the blood sample is centrifuged for 30 minutes at 2000 g at 4° C. The serum is taken off, and exosomes are isolated using precipitation with 10% (v/v) total exosome isolation reagent (Invitrogen; Cat. No. 447.8360) for 30 minutes at 4° C., and centrifugation at 10000 g for 10 minutes. The supernatant is discarded, and the pellet is dissolved in 200 µL PBS. In the next step, the RNA is isolated from the exosomes using a total exosome RNA and protein isolation kit (Invitrogen; Cat. No. 4478545) in accordance with the instructions as provided by the manufacturer.

The RNA as obtained is eluted in 50 µL buffer, and 15 ng of the RNA are then reverse transcribed into cDNA in a reverse transcriptase reaction using specific primers (TaqMan MicroRNA Assay hsa-miR-92, Cat. No. 000430). miR-92a is encoded on chromosome 14 (Chr.14: 115044927-115044508 [+]), and has the following sequence:

(SEQ ID NO. 1)
UAUUGCACUUGUCCCGGCCUG.

cDNA of miR-92a is then quantified using a qPCR. U6 snRNA served as an RNA-reference internal standard (TaqMan microRNA assays U6 snRNA; cat. no. 001973) with the sequence (SEQ ID NO. 2)
GTGCTCGCTTCGGCAGCACATATACTAAAATTGGAACGATACAGAGAAGA

TTAGCATGGCCGCTGCGCAAGGATGACACGCAAATTCGTGAAGCGTTCCA

TATTTT.

Exosomal miRNA is given in Ct-values (Ct (cycle threshold) is a theoretical value indicating the start of the exponential growth of a curve). The delta of the Ct-values of U6 and miR-92a is used in order to conclude on the BAT-activity in patients. The activity in the BAT inversely correlates with the amount of miR-92a, especially in serum-exosomes.

Detection of BAT Activity in Mice miR-34c* directly correlates with the activity of brown/beige fat cell, whereas an inverse correlation was found for miR-92a. The principle of detection is the same as for humans, the primer as used for miR-34c* was (TaqMan MicroRNA Assay mmu-miR-34c* cat. no. 002584). The sequence is AAUCACUAACCACGAGCCAGG (SEQ ID NO. 3) and is localized on chromosome 9: 51103034-51103110 [-]. U6 snRNA also served as a reference.

Results

Brown Adipocytes Release Exosomes

Figure 1A:
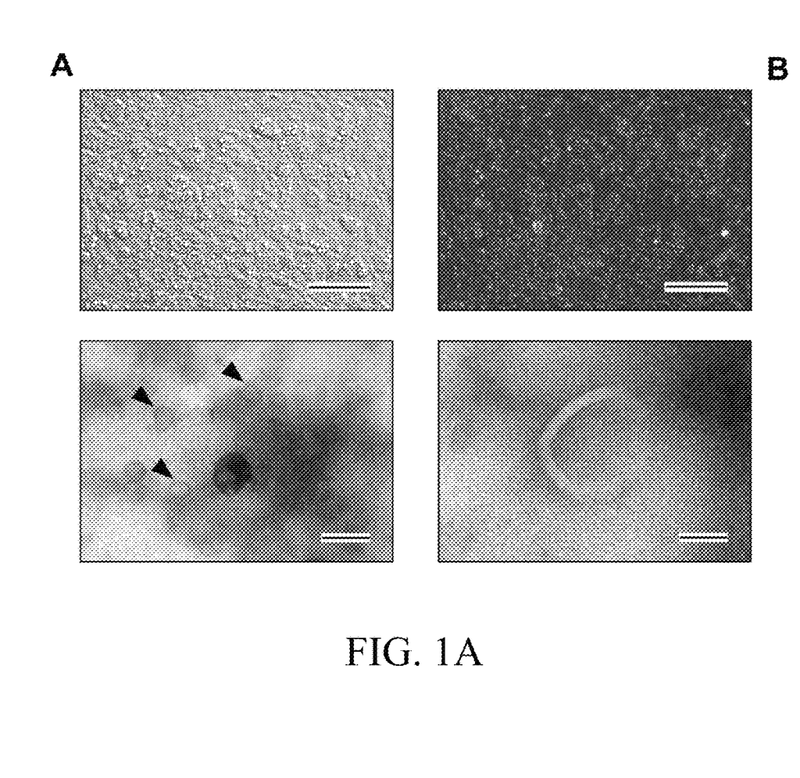
FIGS. 1A-1D. Brown adipocytes secrete exosomes. (1A) Upper lane: Expression of CD63-GFP fusion protein in murine brown adipocytes. Representative bright field (left) and fluorescence image (right) are shown, (Scale bar: 10 µm). Lower lane: Electron microscopy images of exosomes in supernatant of brown adipocytes, (left scale bar: 220 nm, right scale bar: 40 nm). (1B) Representative Western blot of exosome marker protein CD63 and Hsp70 expression in exosomes released from BAT (left panel) and in BAT of mice (right panel). The tissue was treated ex vivo with 10 µM norepinephrine (NE) or without NE (wt), protein isolation buffer sewed as vehicle control. Western blotting of tubulin and cytochrome C (cytC) are shown as loading control and cellular marker. (1C and 1D) ELISA quantification of CD63-positive particles released from cells per mg protein before and after CAMP (200 µM) treatment (1C) and released per mg tissue before and after cold exposure (4° C. for 7 days) (1D). Abbreviations: exo, exosomes; BA, brown adipocytes; PRE, brown pre-adipocytes; beige, beige adipocytes; WA, white adipocytes; Data are presented as mean+/−SD (*p<0.05, p<0.01, *p<0.001, n=3).
Figure 1B:
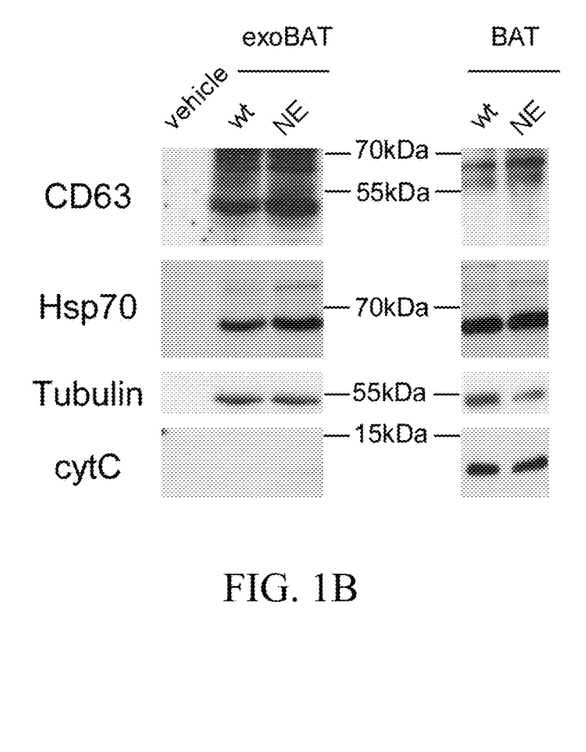
Figure 1C:
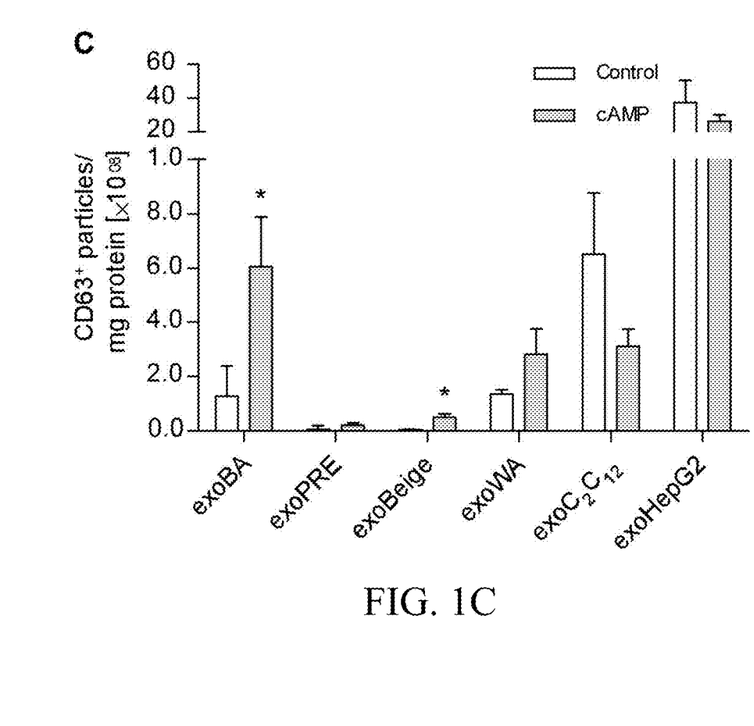
Figure 1D:
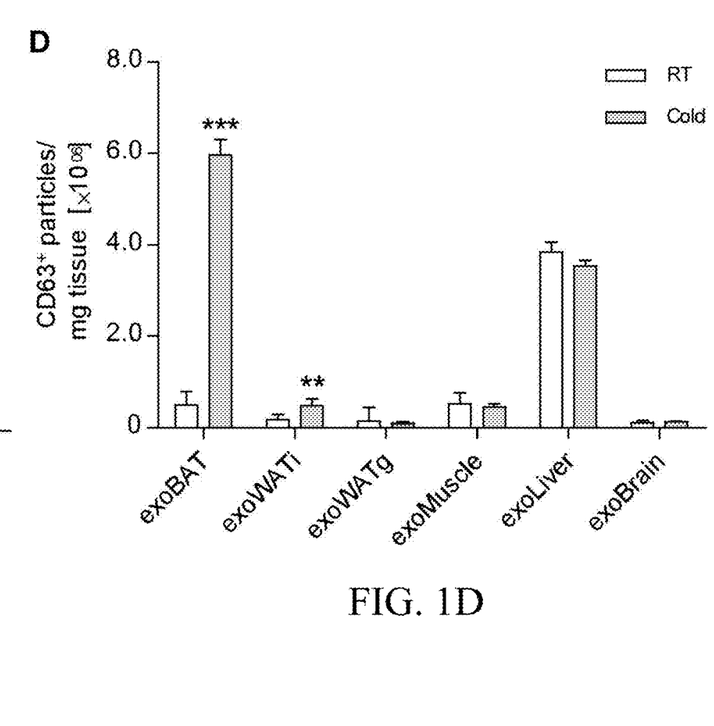

To detect exosomes in brown adipocytes, the inventors initially expressed a GFP fusion protein of the exosome marker (Thery et al., 2002) CD63 in murine brown adipocytes (FIG. 1A). Moreover, the culture medium of brown adipocytes was analyzed for the presence of secreted exosomes using electron microscopy (FIG. 1A) and Western blotting with antibodies against the common exosomal markers CD63 and Hsp70 (FIG. 1B). These data show that brown adipocytes release exosomes. Treatment of brown adipocytes with cAMP, which we used to mimic cold in vitro, resulted in a 4.7-fold increase of exosomes in the culture medium (FIG. 1C) indicating that cAMP signaling enhances exosome release from brown adipocytes. To study exosome release also in beige cells, the inventors treated primary murine white adipocytes with NE, which induced a significant increase in UCP-1 expression. As "pure" white adipocytes, the inventors used 3T3-L1 cells that did not significantly increase UCP-1 expression after NE treatment. cAMP induced a significant increase of exosome release in beige (10.7-fold) adipocytes, but not in white adipocytes or in brown preadipocytes (FIG. 1C). The treatment with cAMP also did not significantly affect the release of exosomes from muscle cells ($C_2C_{12}$) or hepatocytes (HepG2) (FIG. 1C). Similar to the in vitro data, both BAT and inguinal WAT (WATi) of mice showed a significant (9.05-fold and 7.62-fold, respectively) increase in exosome release after cold-exposure (FIG. 1D). WATi was used for the analysis of beige fat, given its high capacity for browning after cold exposure (Seale et al., 2011). In contrast, gonadal WAT (WATg)—the purest white adipose tissue depot (Petrovic et al., 2010)—and other tissues (i.e. muscle, liver and brain) exhibited no significant changes of exosome release after cold-exposure (FIG. 1D). Considering the weight of the three adipose tissues, 87% of the total amount of exosomes is secreted from BAT under cold conditions, whereas exosomes from WATi and WATg make up only 11% and 2%, respectively.

Identification of Exosomal miRNAs in Serum and Release from Brown Adipocytes.

Figure 2A:
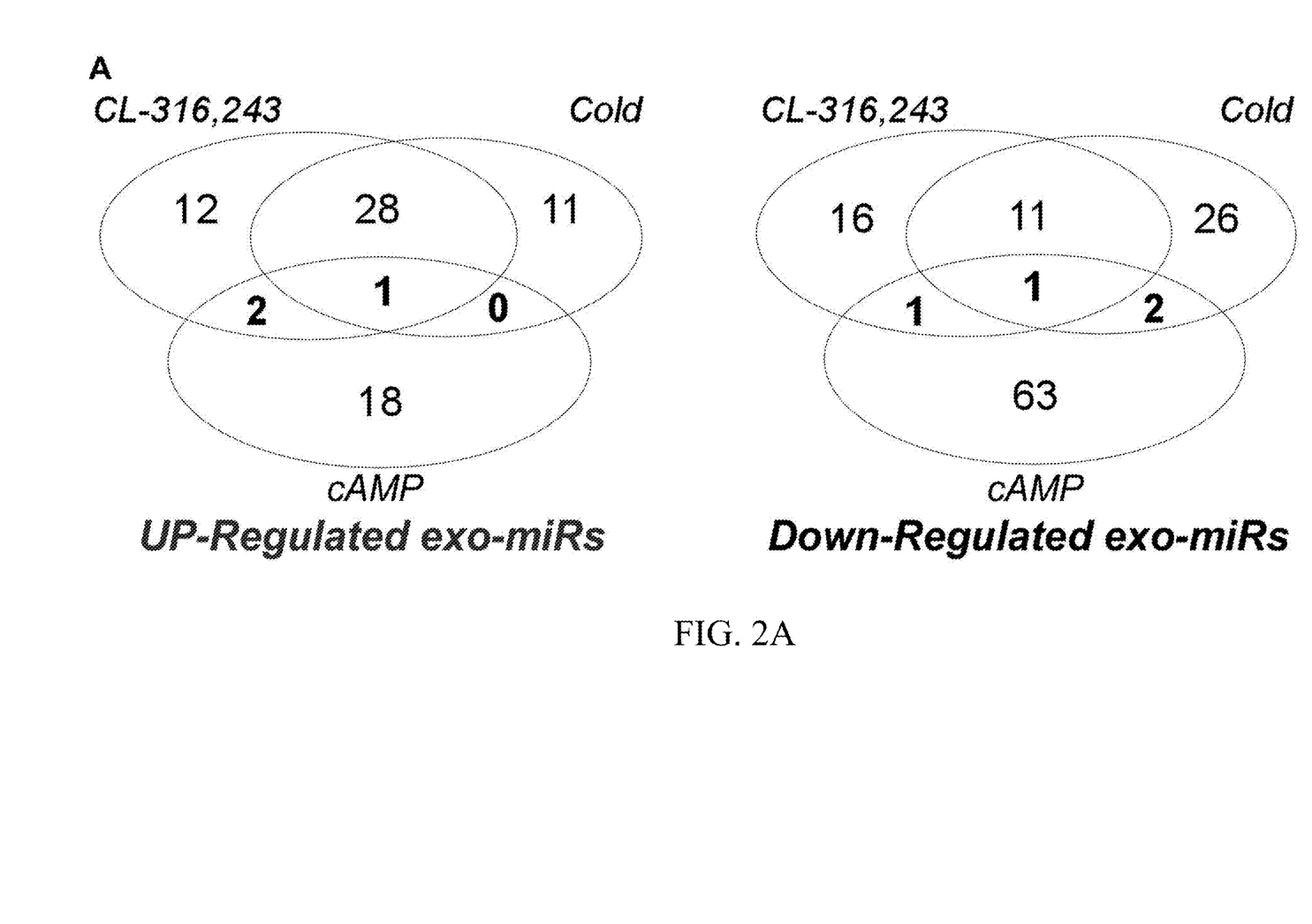
FIGS. 2A-2C. Venn diagram of miRNAs significantly up- or down-regulated in the different models. (2A) Venn diagram showing the overlap of commonly changed miRNAs in mice treated with CL-316,243 or exposed to 4° C. as well as in murine brown adipocytes treated with cAMP (200 µM). (B and C) qPCR validation of changed miRNAs in exosomes released from brown adipocytes (2B) and exosomes present in mouse serum (2C). Data were normalized to U6 expression and presented as mean+/−SEM (*p<0.05, n≥3).

Next, miRNAs were profiled in exosomes isolated from serum of mice with activated BAT—either exposed to cold or treated with the 133-adrenoreceptor agonist CL-316,243 (CL)—and compared to control mice as well as to miRNAs present in exosomes released from brown adipocytes treated with and without cAMP. Based on the expression profiles of the 192 miRNAs that were found in treated mice and brown adipocytes, respectively, the inventors computed an average linking hierarchical clustering. The resulting dendrogram shows a higher similarity of in vitro samples to each other compared to serum samples. To identify miRNAs potentially associated with BAT activation, the inventors visualized the overlap of miRNA expression between the different groups by Venn diagrams (FIG. 2A). Among 757 profiled miRNAs, 41 miRNAs were found to be differentially expressed in both in vivo groups with 12 and 29 miRNAs that were up- and downregulated, respectively (FIG. 2A).

Figure 2B:
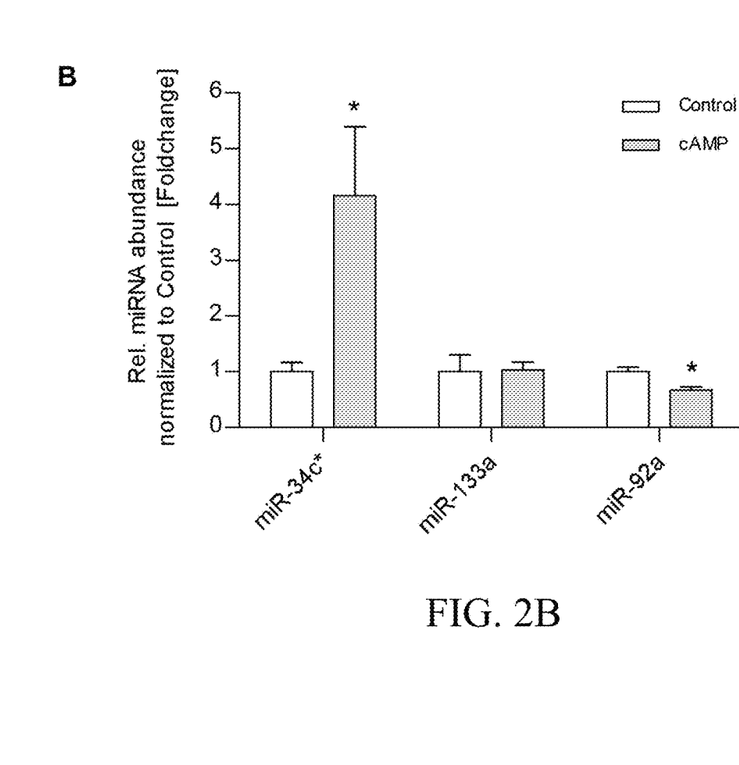
Figure 2C:
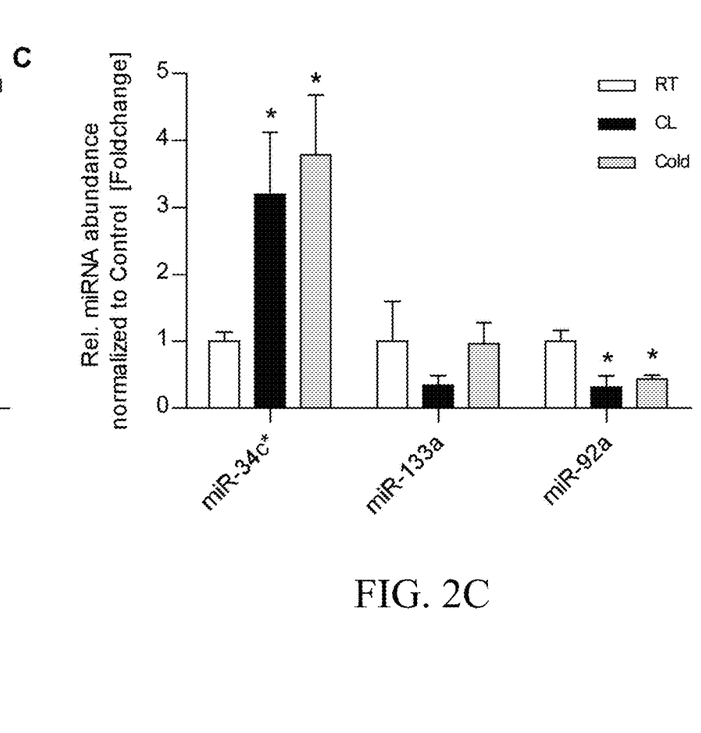

Two miRNAs—miR-133a and miR-34c*—were differentially regulated in serum exosomes upon cold-exposure and CL treatment in vivo as well as in exosomes released by activated brown adipocytes in vitro (FIG. 2A). For further validation, the inventors focused on miR-133a and miR-34c* as well as on miR-92a as an additional miRNA candidate, because miR-92a exhibited the highest change in exosomes of cells treated with cAMP as compared to exosomes from untreated cells. Quantitative real-time PCR (qPCR) revealed that miR-34c* and miR-92a were significantly up- and down-regulated, respectively, in the exosomes from cAMP treated brown adipocytes and from serum of mice with active BAT (FIGS. 2, B and C). Although miR-133a was down-regulated in serum-derived exosomes of CL-treated mice, miR-133a expression was neither significantly altered in brown adipocyte-derived exosomes nor in any of the mouse models analyzed (FIG. 2, B and C). Comparison of the abundance of these miRNAs in exosomes and in brown adipocytes revealed that miR-92a and miR-34c* were differentially expressed after cAMP treatment in the exosomes but not in the cells. Although miR-34c* is differentially expressed during differentiation of murine brown adipocytes (Keller et al., 2011), miR-34c* was not detectable in human serum samples.

Therefore, the inventors focused on miR-92a in their further studies. miR-92a levels in exosomes released from cAMP-stimulated brown adipocytes were reduced after 4 h, and a significant reduction was observed after 24 h. To identify the source of miR-92a in mice, the inventors quantified the amount of miR-92a in exosomes isolated from BAT, WATi, WATg, skeletal muscle, liver and brain, miR-92a was detectable in all tested samples. The highest abundance of miR-92a per exosome was released by WATi followed by WATg, BAT, liver brain and muscle. Cold exposure induced a significant down-regulation of exosomal miR-92a in BAT (to 6% of the control) and WATi (to 18%), but not in exosomes derived from other tissues. Similar changes were observed in vitro. In mice, the increase in BAT mass upon prolonged cold-exposure significantly correlated with the reduction of miR-92a abundance in serum.

Exosomal miR-92a Correlates with Human BAT Activity

For the analysis of human exosomal miRNAs, the inventors focused on miR-92a and miR-133a, whereas miR-34c* was not detectable in human serum exosomes. Although miR-92a and miR-133a expression levels showed considerable inter-individual variation, their expression was not different between males and females and was not related to any other basal subject characteristics such as age, weight or Body-Mass-Index (BMI).

Figure 3A:
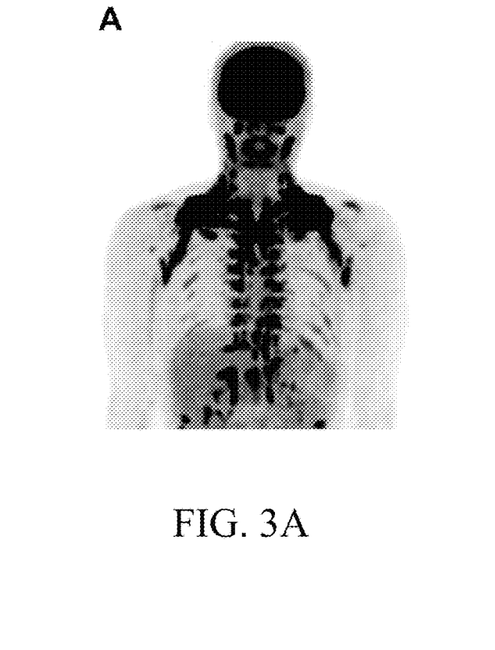
FIGS. 3A-3E. Correlation of exosomal miR-92a in serum with BAT activity in humans. (3A and B) 18F-FDG PET/CT image of a subject with high (3A) and low (3B) BAT activity. (3C) miR-92a expression as quantified by qPCR. Data were normalized to U6, and expressed as mean+/− SEM. (*p<0.05, n=11 per group). (3D) $Log_{10}$ miR-92a value is negatively related to BAT SUVmean value when considering the whole group (p=0.019, n=22). (3E) Changes in miR-92a expression levels (Delta $log_{10}$ miR-92a value) tended to correlate with changes in BAT activity (Delta BAT SUVmean value) upon a 10-day cold acclimation period (p=0.11; n=10). See also Table 1.
Figure 3B:
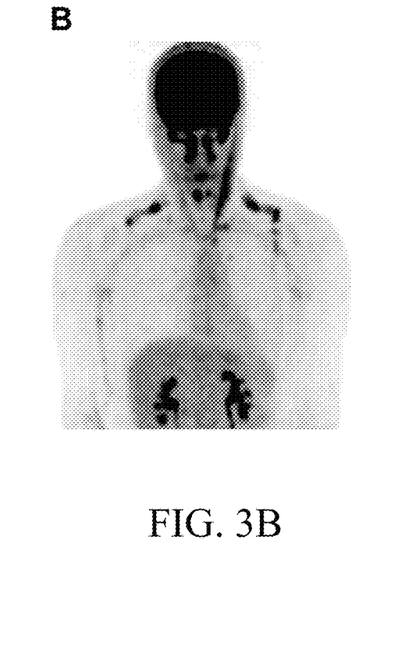
Figure 3C:
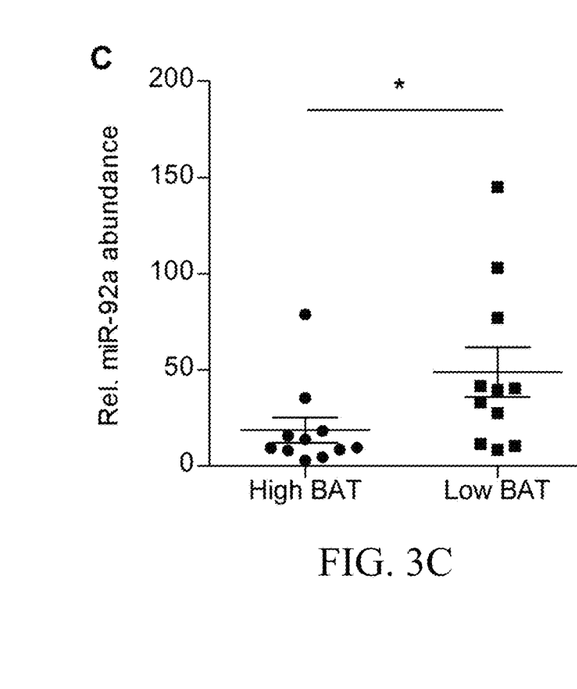
Figure 3D:
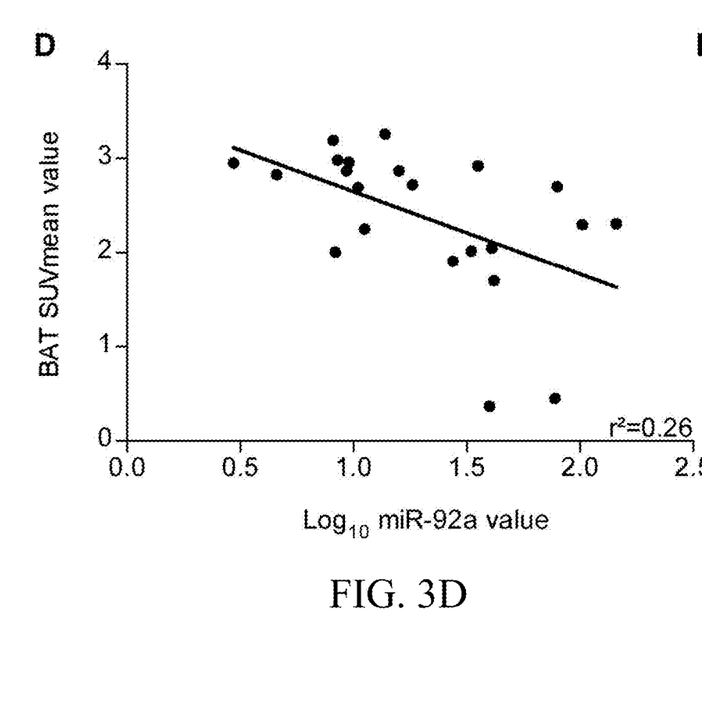

Based on PET/CT data (FIGS. 3, A and B), subjects were initially divided into a "low BAT" (mean standard uptake value (SUVmean)<median SUV [2.70]) and "high BAT" (SUVmean>median SUV [2.70]) group (n=11 per group; Table 1). Interestingly, miR-92a expression was significantly lower in the high BAT group compared to the low BAT group (p=0.018, FIG. 3C), whereas miR-133a expression was similar between groups (p=0.757). In addition, when considering the group as a whole, the inventors observed a significant negative correlation between $\log_{10}$ miR-92a and the BAT SUVmean value (FIG. 3D). Such correlation was absent for miR-133a. In a stepwise multivariable linear regression analysis with $\log_{10}$ miR-92a as dependent variable, and age, sex, BMI, fat percentage and BAT SUVmean as independent variables, BAT SUVmean was the only independent predictor of $\log_{10}$ miR-92a. In addition, individual univariate analyses showed no relations between these other parameters and $\log_{10}$ miR-92a.

Figure 3E:
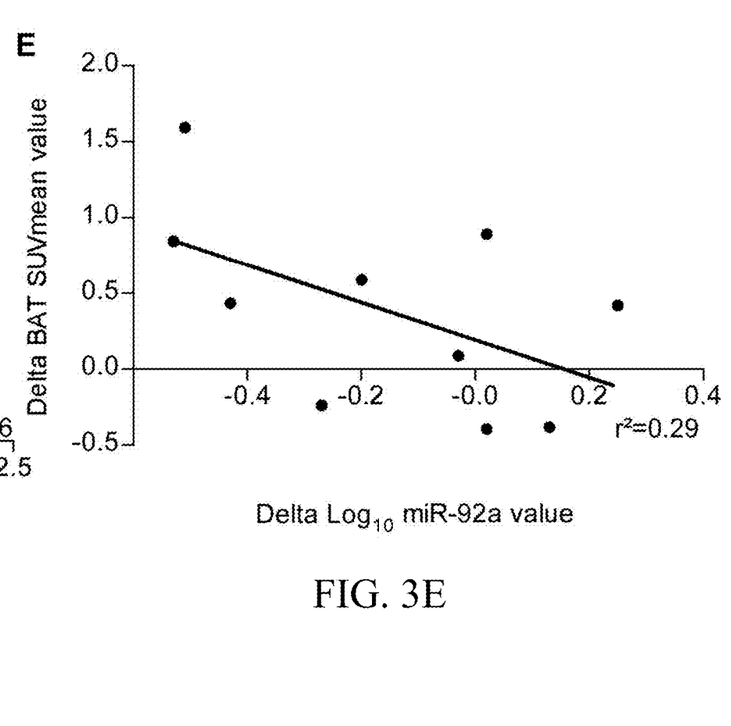

Ten subjects were subsequently exposed to a 10-day cold acclimation period, which caused a recruitment of BAT and an increase in non-shivering thermogenesis, as described previously (van der Lans et al., 2013). Interestingly, miR-92a abundance tended to be lower after this cold acclimation period (19.5+/−4.1 vs. 13.8+/−4.0; mean+/−SEM) and the change in rniR-92a levels tended to be negatively related to changes in BAT activity ($r^2$=0.29, p=0.11, FIG. 3E) upon this cold acclimation period. Moreover, the inventors analyzed miR-92a levels in serum exosomes of subjects that were acutely exposed to cold (ca. 1-1.5 h). Interestingly, serum $\log_{10}$ miR-92a levels of these acute cold exposed samples also tended to inversely correlate with BAT SUVmean. Taken together, the abundance of exosomal miR-92a in the samples, such as serum, clearly negatively correlated with BAT activity not only in mice, but also in human subjects.

REFERENCES

Analitis, A., et al. (2008). Effects of cold weather on mortality: results from 15 European cities within the PHEWE project. Am J Epidemiol 168, 1397-1408.

Barter, A., et al. (2011). Brown adipose tissue activity controls triglyceride clearance. Nat Med 17, 200-205.

Bhaskaran, K., et al. (2009). Effects of ambient temperature on the incidence of myocardial infarction. Heart 95, 1760-1769.

Bordicchia, M, et al. (2012). Cardiac natriuretic peptides act via p38 MAPK to induce the brown fat thermogenic program in mouse and human adipocytes. J Clin Invest 122, 1022-1036.

Brase, J. C., et al. (2010). Serum microRNAs as non-invasive biomarkers for cancer. Mol Cancer 9, 306.

Cannon, B., et al. (2004). Brown adipose tissue: function and physiological significance. Physiol Rev 84, 277-359.

Chen, Y., et al. (2013). miR-155 regulates differentiation of brown and beige adipocytes via a bistable circuit. Nat Commun 4, 1769.

Cheng, L., et al. (2014). Emsomes provide a protective and enriched source of miRNA for biomarker profiling compared to intracellular and cell-free blood. Journal of extracellular vesicles 3- 23743.

Cortez, M. A., et al. (2011). MicroRNAs in body fluids the mix of hormones and biomarkers. Nature reviews. Clinical Oncology 8, 467-477.

Cypess. A M., et al. (2009). Identification and importance of brown adipose tissue in adult humans. N Engl J Med 360, 1509-1517.

Cypess, A. M., et al. (2013). Anatomical localkation, gene expression profiling and functional characterization of aduk human neck brown fat. Nat Med 19, 635-639.

Frontini. A., et al. (2010). Distribution and development of brown adipocytes in the murine and human adipose organ. Cell Metab 11.253-256.

Gnad, T., et al. (2014). Adenosine activates brown adipo-se tissue and recruits beige adipocytes via A2A receptors. Nature 516, 395-399.

Hanssen, M. J., et al. (2015). Glucose uptake in human brown adipose tissue is impaired upon fasting-induced insulin resistance. Diabetologia 58, 586-595.

Harms, M., et al. (2013). Brown and beige fat: development, function and therapeutic potential. Nat Med 19, 1252-1263.

Jespersen, N. Z., et al. (2013). A classical brown adipose tissue mRNA signature partly overlaps with brite in the supraclavicular region of adult humans. Cell Metab 17 798-805.

Kajimura, S., et al. (2013). A New Era in Brown Adipose Tissue Biology: Molecular Control of Brown Fat Development and Energy Homeostasis. Annu Rev Physiol 76, 225-249.

Keller, P., et al. (2011). Gene-chip studies of adipogenesis-regulated microRNAs in mouse primary adipocytes and human obesity. BMC endocrine disorders 11, 7.

Lo. K. A., et al. (2013). Turning WAT into BAT: a review on regulators controlling the browning of white adipocytes. Biosci Rep 33.

Mitschke, M. M., et al. (2013). Increased cGMP promotes healthy expansion and browning of white adipose tissue. FASEB J 27, 1621-1630.

Nedergaard, J., et al. (2007). Unexpected evidence for active brown adipose tissue in adult humans. Am J Physiol Endocrinol Metab 293, E444-452.

Ng, M., et al. (2014). Global, regional, and national prevalence of overweight and obesity in children and adults during 1980-2013. a systematic analysis for the Global Burden of Disease Study 2013 Lancet 384,766-781.

Nguyen, K. D., et al. 1201 1). Alternatively activated macrophages produce catecholamines to sustain adaptive thermogenesis. Nature 480, 104-108.

Petrovic, N., et al. (2010). Chronic peroxisome proliferator-activated receptor gamma (PPARgamma) activation of epididymally derived white adipocyte cultures reveals a population of thermogenically competent, UCPI-containing adipocytes molecularly distinct from classic brown adipocytes. J Biol Chem 285, 7153-7164.

Pfeifer, A., et al. (2014). Brown, Beige, and White: The New Color Code of Fat and Its Pharmacological Implications. Annu Rev Pharmacol Toxicol. 16

Rosen, E. D., et al. (2014). What we talk about when we talk about fat. Cell 15620-44.

Rosenfeld, N., et al. (2008). MicmRNAs accurately identify cancer tissue origin. Nat Biotechnol 26, 462-469.

Saito, M., et al. (2009). High incidence of metabolically active brown adipose tissue in healthy adult humans: effects of cold exposure and adiposity. Diabetes 58, 1526-1531.

Seale, P., et al. (201 1). Prdm16 determines the thermogenic program of subcutaneous white adipose tissue in mice. J Clin Invest 121, 96-105.

Shabalina, I. G., et al. (2013). UCP1 in br'ielbeige adipose tissue mitochondria is functionally thermogenic. Cell Rep 5, 1196-1203.

Sharp, L. Z., et al. (2012). Human BAT possesses molecutar signatures that resemble beige/brite cells. PLoS One 7, e49452.

Thery C., et al. (2002). Exosomes: composition, biogenesis and function. Nat Rev Immunol 2, 569-579.

Trajkovski, M., et al. (2012). MyomiR-133 regulates brown fat differentiation through Prdm16. Nat Cell Biol 14. 1330-1335.

Trajkovski, M., et al. (2013). MicroRNA networks regulate development of brown adipocytes. Trends Endocrinol Metab 24, 442-450.

van der Lans, A. A., et al. (2013). Cold acclimation recruits human brown fat and increases nonshivering thermogenesis. J Clin Invest 123.3395-3403.

van der Lans, A. A., et al. (2014). Cold-activated brown-adipose tissue in human adults: methodological issues. Am J Physiol Regul Integr Comp Physiol 307; R103-5.r 13.

van Marken Lichtenbelt, W. D., et al. (2009). Cold-activated brown adipose tissue in healthy men. N Engl J Med 360, 1500-1508.

van Niel, G., et al. (2006). Exosomes: a common pathway for a specialized function. Journal of biochemistry 140, 13-21.

Virtanen, K. A., et al (2009). Functional brown adipose tissue in healthy adults. N Engl J Med 360, 1518-1525.

Walden, T. B., et al. (2009). Distinct expression of muscle-specific microRNAs (myomirs) in brown adipocytes. J Cell Physiol 218, 444-443.

Wu, J., et al. (2012). Beige adipocytes are a distinct type of tbrmogenic fat cell in mouse and human. Cell 150366-376.

The invention claimed is:

1. A method for identifying a compound that promotes or reduces the activation and/or activity of a brown/beige fat cell or brown/beige adipose tissue (BAT) of a patient, comprising:
   a) obtaining a biological sample containing BAT of the patient,
   b) contacting a candidate compound with BAT in the biological sample,
   c) detecting the amount of miR-92 in exosomes derived from said BAT, and
   d) identifying a compound that promotes or reduces the activation and/or activity of BAT based on the amount of said miR-92 detected in response to said candidate compound.

2. The method according to claim 1, wherein said amount of said miR-92 as produced is compared with miR-92 in a non-activated BAT or a BAT before the contacting step.

3. A method for producing a pharmaceutical composition, comprising performing a method according to claim 1, and formulating said compound as identified into a pharmaceutical composition.

4. The method according to claim 1, wherein said compound as identified is selected from a small chemical molecule, a peptide, and an antibody or a fragment thereof.

5. The method according to claim 4, wherein the antibody or fragment thereof is a monoclonal, polyclonal, human, humanized, and/or a recombinant antibody, or a functional fragment thereof.

6. The method according to claim 1, wherein the measuring in step b) comprises at least one method selected from nucleic acid reverse transcription, amplification, and detection.

7. The method according to claim 1, wherein the measuring in step b) comprises PCR.

8. The method according to claim 1, wherein the amount of miR-92 derived from said BAT as measured in step b) negatively correlates with the activation and/or activity of said BAT.

9. The method according to claim 1, wherein said activation and/or activity of said BAT is induced independently from temperature (thermoneutrality).

10. The method according to claim 1, wherein the patient is suffering from an obesity-related disease, diabetes, a cardiovascular disease, and/or stroke.

* * * * *

SEQUENCE LISTING

```
<160> NUMBER OF SEQ ID NOS: 3

<210> SEQ ID NO 1
<211> LENGTH: 21
<212> TYPE: RNA
<213> ORGANISM: homo sapiens

<400> SEQUENCE: 1
uauugcacuu gucccggccu g                                           21

<210> SEQ ID NO 2
<211> LENGTH: 106
<212> TYPE: DNA
<213> ORGANISM: homo sapiens

<400> SEQUENCE: 2
gtgctcgctt cggcagcaca tatactaaaa ttggaacgat acagagaaga ttagcatggc    60
cgctgcgcaa ggatgacacg caaattcgtg aagcgttcca tatttt                 106
```

```
<210> SEQ ID NO 3
<211> LENGTH: 21
<212> TYPE: RNA
<213> ORGANISM: Mus musculus

<400> SEQUENCE: 3
aaucacuaac cacgagccag g                                               21
```